United States Patent
Sayet et al.

(10) Patent No.: US 6,319,191 B1
(45) Date of Patent: *Nov. 20, 2001

(54) IMPLANTABLE BODY FLUID FLOW CONTROL DEVICE

(75) Inventors: Peter H. Sayet, Sunny Isles; Lloyd A. Sutherland, Boca Raton; Victor Politano, North Miami, all of FL (US)

(73) Assignee: Precision Medical Devices, Inc., Fort Lauderdale, FL (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/048,823

(22) Filed: Mar. 26, 1998

(51) Int. Cl.$^7$ .............................. A61F 2/00; A61F 2/02; A61B 17/08
(52) U.S. Cl. .............................. 600/29; 600/30; 606/151
(58) Field of Search ................ 600/29–31; 606/151–157

(56) References Cited

U.S. PATENT DOCUMENTS

| | | |
|---|---|---|
| 3,357,434 | 12/1967 | Abell . |
| 3,419,008 * | 12/1968 | Plishner ................................. 600/31 |
| 3,924,631 | 12/1975 | Mancusi, Jr. . |
| 3,926,175 | 12/1975 | Allen et al. . |
| 4,024,855 | 5/1977 | Bucalo . |
| 4,053,952 | 10/1977 | Goldstein . |
| 4,352,960 | 10/1982 | Dormer et al. . |
| 4,387,705 * | 6/1983 | Finney ................................. 600/30 |

(List continued on next page.)

FOREIGN PATENT DOCUMENTS

| | | |
|---|---|---|
| 1566202 | 9/1969 | (FR) . |
| 2658084 | 2/1990 | (FR) . |
| 2688693 | 3/1992 | (FR) . |
| 2769491 | 10/1997 | (FR) . |
| 1174814 | 2/1967 | (GB) . |
| WO 87/07132 | 12/1987 | (WO) . |
| WO 92/16162 * | 10/1992 | (WO) . |
| WO 98/23232 * | 6/1998 | (WO) . |

OTHER PUBLICATIONS

English abstract of FR 2688693—One Page.
English abstract of FR 2658084—One Page.
Derwent Summary for EP 1023002A1: Artificial Sphincter with Magnetic Control—Two Pages.

*Primary Examiner*—Robert L. Nasser
*Assistant Examiner*—Navin Natnithithadha
(74) *Attorney, Agent, or Firm*—Akerman, Santerfitt & Eidson, P.A.

(57) ABSTRACT

An apparatus for controlling fluid flow within a host body has a first shell and a second shell for coupling with the second shell to form a cylindrical object suitable for engaging and surrounding a selected canal with the host body. The cylindrical object is open at both ends and has an interior diameter of a dimension making it suitable for fitting over the selected host body's canal, such as the urethra. The apparatus also includes a plunger for constricting the fluid flow when activated. The plunger may be activated by an electrical solenoid or hydraulic or pneumatic activation to move from a free-flow position into a constricting position wherein the fluid flow though the canal is substantially prevented or reduced. The apparatus can be used for controlling incontinence or restricting fluid flow in other body canals. The host-user can activate the apparatus with a remote control device outside the body which communicates with the implanted apparatus by means of any wireless communication that transmits a signal to the device causing the solenoid to move the plunger into the constricting position. A second signal causes the plunger to retract into a free-flow position when the user no longer feels the urge to urinate.

30 Claims, 4 Drawing Sheets

U.S. PATENT DOCUMENTS 4,553,271 11/1985 Baker .
4,777,949 10/1988 Perlin .
4,994,019 2/1991 Fernandez et al. .
5,509,888 * 4/1996 Miller ..................................... 600/29
5,562,598 10/1996 Whalen et al. .

* cited by examiner

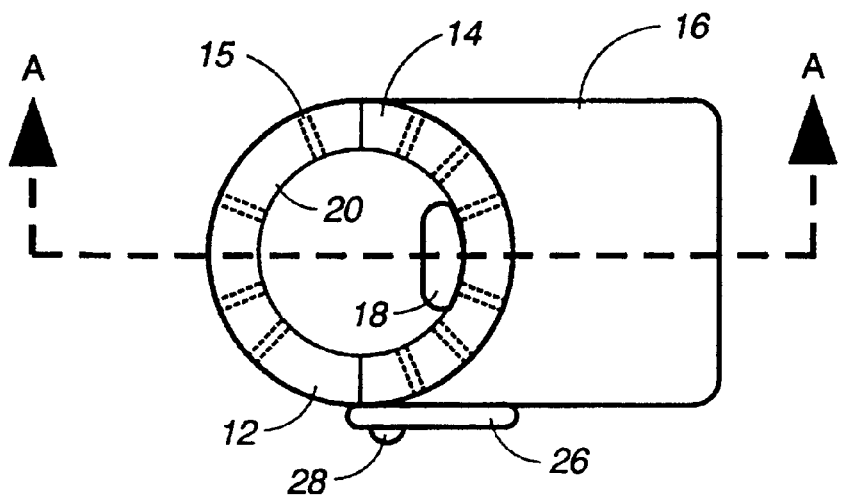
FIG. 2
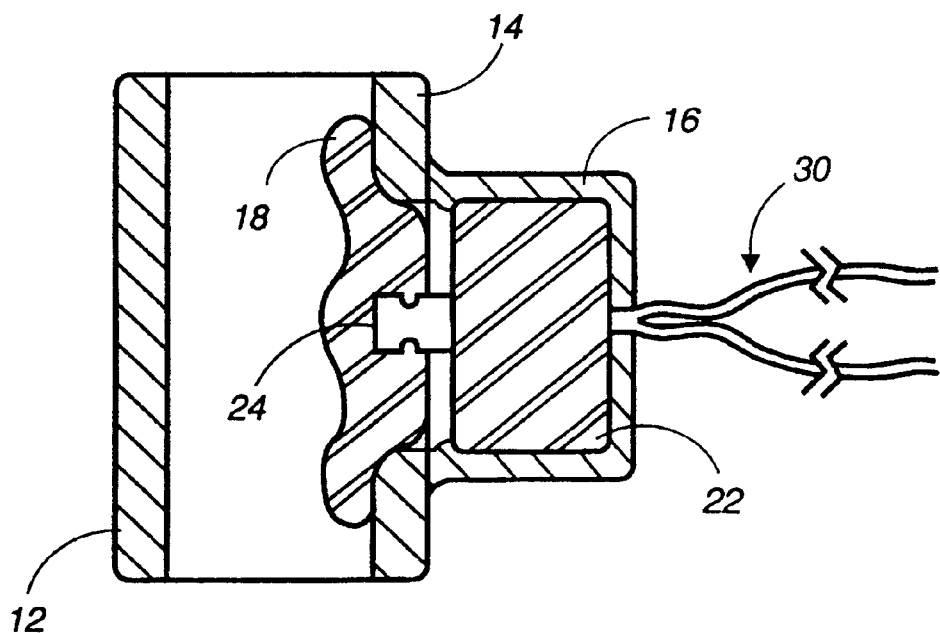
FIG. 3 (SECTION A-A)

IMPLANTABLE BODY FLUID FLOW CONTROL DEVICE

CROSS-REFERENCE TO RELATED APPLICATIONS

Not applicable.

BACKGROUND OF THE INVENTION

1. Field of the Invention

The invention disclosed broadly relates to the field of medical devices, and more particularly relates to the field of devices for the control of fluid flow within the urethra.

2. Description of the Related Art

Incontinence is a condition wherein persons lose control over their voluntary, urinary function. The condition can arise from various causes. These causes include a variety of related and unrelated diseases, aging, and deterioration of the voluntary urethra sphincter muscle. The costs and inconvenience to persons suffering from this condition are great. Several remedies exist for this that are known in the prior art. Among these, the most common are surgical corrections (minor and major), drugs, and devices which serve to capture discharges (i.e., "capture" or diaper systems). Another solution is to place a patch over the urinary orifice to prevent unwanted discharge. Possibly the most effective solution to date is the use of artificial sphincters. These devices are surgically installed and are hydraulically or pneumatically driven, operating by inflation of ballasts to suppress fluid flow. However, control of these devices is not always easy and is often inconvenient. Accordingly, there is a need for an improved method and apparatus to control the urinary function.

SUMMARY OF THE INVENTION

Briefly, in accordance with the invention, an implantable apparatus for controlling fluid flow within a host body comprises: engaging means for engaging a canal within the body, said canal having a diameter; constricting means for reducing the diameter of the canal; and control means for causing the constriction means to reduce the diameter of the canal.

BRIEF DESCRIPTION OF THE DRAWINGS

FIG. 2 is a front view of a body fluid flow control device in a closed position.

FIG. 3 is a cross section of the device shown in FIG. 2.

DETAILED DESCRIPTION OF AN EMBODIMENT

Figure 1:
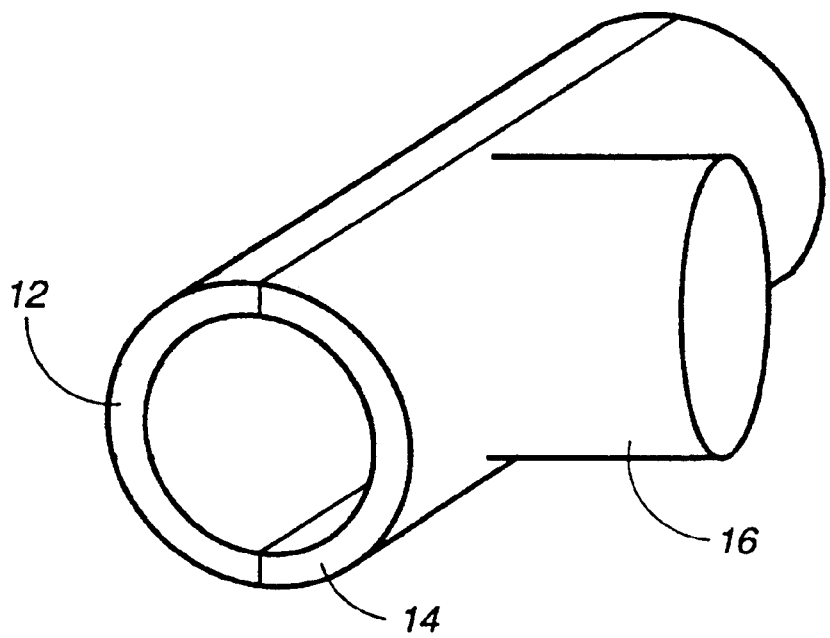
FIG. 1 is an oblique view of a fluid flow control device according to the present invention.

Referring to FIG. 1, there is shown an oblique view of a body fluid flow control device 10 according to the invention. The device 10 has many possible applications including use as a remedy for incontinence.

The fluid flow control device 10 is a two piece assembly comprising a hollow cylindrical shape formed by coupling a first cylinder casing shell 12 and a second cylinder casing shell 14. When the first shell 12 is coupled with the second shell 14, there is assembled a cylindrical tube with an inner diameter 20 which is well suited for fitting around a host body canal (i.e., any tube within the human body) such as the urethra. The device 10 is designed such that it engages the canal through which flow is to be controlled. The device also comprises a casing 16 containing a piston-like mechanism for driving a plunger (shown in other Figures) into the hollow portion of the device to restrict fluid flow through the canal enveloped by the device 10. The piston-like mechanism is preferably an electromechanical solenoid but any hydraulic, pneumatic, or equivalent piston-like mechanism can be used.

A surgeon would introduce the device 10 into a host by making an incision providing access to the urethra. This is done according to a commonly used surgical protocol for exposing and "freeing" the urethra from its surrounding tissue. The removal of sphincter muscle is optional to the surgeon. Then cylinder shells 12 and 14 are placed around the exposed and freed portion of the urethra with the hinged side of the device 10 being placed on the back side of the urethra. The device 10 is locked into a closed position. The device 10 is then anchored in place by suturing the urethra (in that area) using a surgical grade mesh embedded in the device's bottom collar. Once this is done the host can be "closed up" and the device 10 can then be controlled remotely from outside the host.

Referring to FIG. 2, there is shown a front view of the device 10. The device 10 is in the closed position such that portion 12 is locked with portion 14 by means of a hinge lock comprising a strap 26 and snap pin 28. Any other equivalent locking means can also be used for this purpose.

Figure 6:
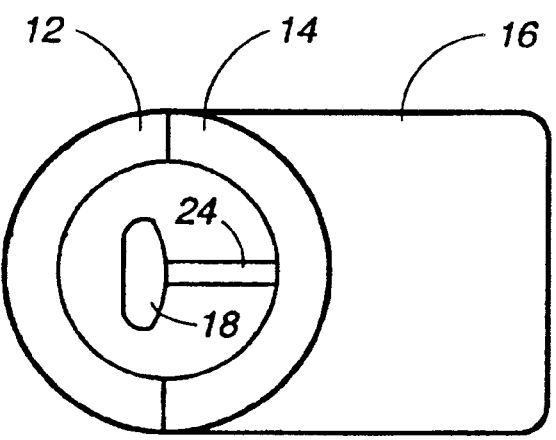
FIG. 6 is a front view of the device with the plunger in a constricting position.

In the preferred embodiment, the device 10 forms a hollow cylinder having an inner diameter 20 adapted to fit over the canal to be constricted. When designed as an incontinence remedy, the dimension of the diameter is controlled by that of the urethra. Portion 14 also includes a casing 16 for an electromechanical solenoid (shown in FIG. 3). The solenoid moves a plunger 18 from a free flow (or retracted) position (shown in FIG. 2) to a constricting (extended) position (shown in FIG. 6).

The device 10 comprises a plurality of holes or portals 15 (shown in broken lines) to allow for fluid flow into the inner portion of the device 10 allowing additional tissue growth in and around the area occupied by the device 10. The holes are preferably 0.031 inches in diameter and are randomly located. However, other dimensions can also be effective. This tissue growth provides additional anchoring support and prevents necrosis of the affected original tissue in the area.

Referring to FIG. 3, there is shown a cross section taken along line 3—3 in FIG. 2. This view reveals the structure of a piston-like contricting device with a plunger 18 attached to a shaft 24 activated by the solenoid 22. The plunger presses against the urethra while the other side of the device 10 acts as a "back wall" to restrict or prevent fluid flow. The plunger 18 can be electronically activated in a series of increased power surges such that the device 10 can be programmed to open or close via a series of ever increasing (or decreasing) stepping motions. The plunger 18 is designed with ridges that provide three pressure points against the urethra. As in the case of the holes 15, this structure prevents necrosis of the affected tissue and affords more positive fluid shut off.

A pair of teflon-coated electrical wires 30 are used to conduct electrical current into the solenoid to activate the movement of the plunger 18. Lead wires will run (internally) from the internally installed device 10 to the internally installed "switching" mechanism and power supply 50 (shown in FIG. 7). The connection of wires 30 is made such that the entry points of the wires into the device 10 are hermetically sealed to prevent fluid from entering into device 10. The implantation site of the power supply (e.g., batteries) is such that the power supply can be replaced with a simple outpatient procedure using only local anesthetic.

Figure 4:
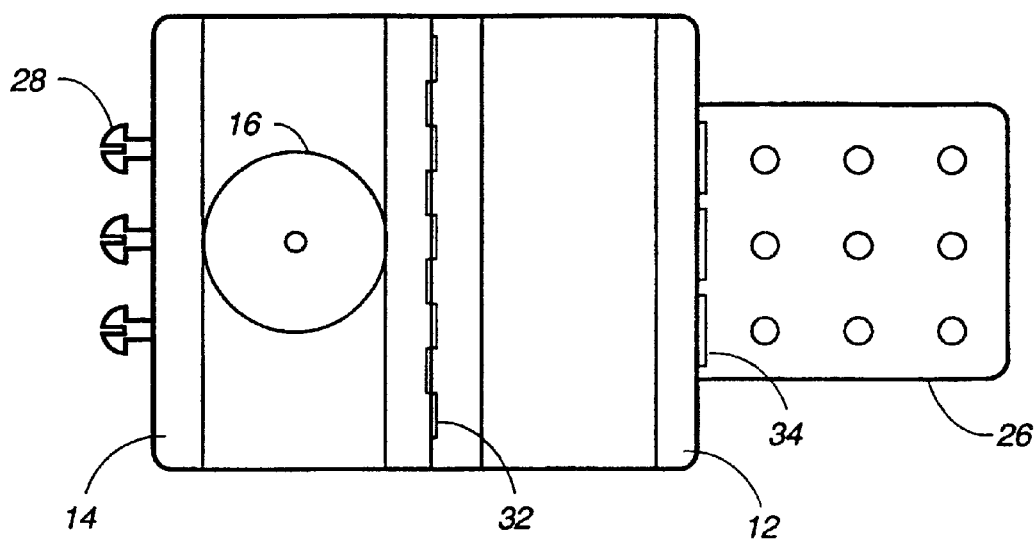
FIG. 4 is a top view of a device in an open position according to the present invention.
Figure 5:
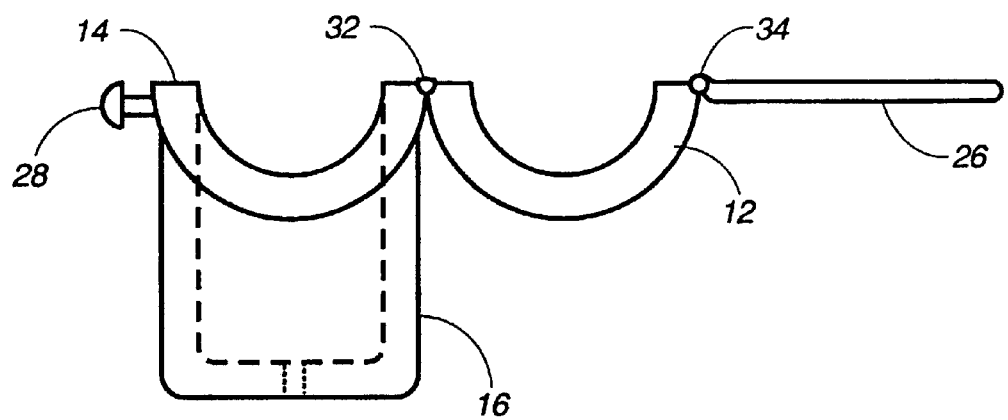
FIG. 5 is a front view of the device in its open position.

Referring to FIGS. 4 and 5, the open position of the device 10 is illustrated. When the device 10 is first introduced into a host, it is in the open position to enable the engagement of the device to the urethra. FIG. 4 is a top view of an open device 10. Device portion 14 is pivotally attached to portion 12 by means of a hinge 32 and can be locked into the closed position by pivoting the two halves together and then snapping the clamp 26 into snapping pins 28 (which are aligned to their corresponding holes in the clamp 26). The clamp 26 is pivotally attached to the shell 12 by means of a hinge 34. In another embodiment, portion 12 would not be pivotally attached to portion 14 but could be placed together and then clamped into place with two clamps such as clamp 26, or other equivalent means. Moreover, any known locking means having the desired function can also be used.

The device 10 is preferably made from a light, corrosion-resistant material such as durable inert plastics or stainless steel, chosen to maximize its useful life. The casing must be impervious to liquids. The device 10 is powered by a power supply installed in a nearby area of the lower abdomen and is controlled by a switch embedded in the subcutaneous wall of the patient's abdomen. The switch is operated by an external triggering unit commanded by the patient.

Although the device 10 is shown having a cylindrical shape, it can comprise any other shape that is suitable for engaging an interior body tube such as the urethra. Moreover, the device 10 can be designed in other embodiments to engage other body tubes or canals. Thus, other possible applications for devices in accordance with the invention include a reversible vasectomy device, a nutrition absorbtion device, or a reversible nutrition absobtion device to treat extreme obesity.

Figure 7:
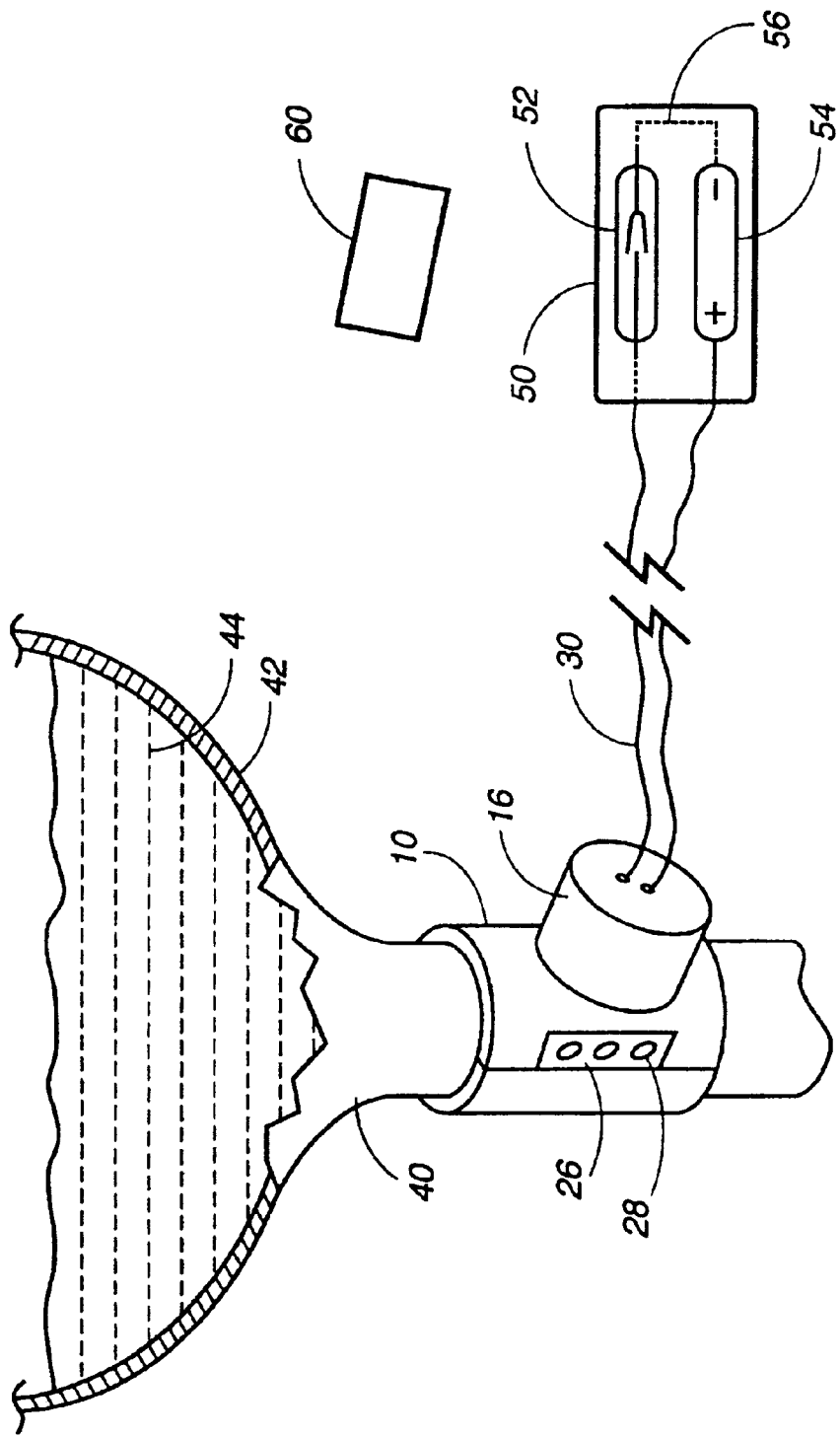
FIG. 7 is an illustration of a device according to the invention shown engaging a human urethra.

Referring to FIG. 7, there is shown an illustration of the device 10 engaging a urethra 40. The device 10 preferably surrounds the urethra in the general location of the sphincter muscle. The urethra is part of the urinary tract which also comprises a bladder 42 which contains liquid waste matter 44. The device 10 is coupled to a control device 50 which comprises a reed switch 52 that is controlled from a magnetic device 60 outside the host body. The device 50 is hermetically sealed and preferably has a Silicon casing. The control device 50 also comprises a battery 54 which is easily removable and replacable. The device 10 may comprise a number of triggering mechanism options from a touch sensor to infrared, voice or sound activation. Any of several well-known control devices can be used to control the operation of device 10 by a user. As mentioned above, the device 10 is surgically implanted into a human host such that the host will require a control mechanism that can be operated from outside the host. One simple example would be a switch implanted just underneath the host's skin such that the host can activate it by pressing on the skin above the switch. Any of several known pressure-activated switches will do provided that they are made from a suitable corrosion resistant material. Another control mechanism could be a smart card having a coil or other means for generating electromagnetic signals that control a control device inside the host.

Although a specific embodiment of the invention has been disclosed, it will be understood by those having skill in the art that changes can be made to this specific embodiment without departing from the spirit and scope of the invention. The scope of the invention is not to be restricted, therefore, to the specific embodiment, and it is intended that the appended claims cover any and all such applications, modifications, and embodiments within the scope of the present invention.

What is claimed is:

1. An implantable apparatus for controlling fluid flow through a canal within a host body without having to sever the canal (i) to implant said implantable apparatus inside the host body or (ii) to operate said implantable apparatus following implantation thereof, said implantable apparatus comprising:

a hollow housing for positioning around a selected area of a canal within the host body;

an electrically operated piston comprising a slidable shaft connected to a plunger positioned within said hollow housing for driving the plunger to an extended position and for retracting the plunger to a retracted position; and a control device for selectively moving said electrically operated piston between the extended position to constrict a portion of the selected area of the canal to reduce or stop fluid flow through the canal and the retracted positioned to open the constricted portion of the selected area of the canal to permit fluid flow through the canal to control fluid flow through the canal.

2. An implantable apparatus of claim 1 wherein said hollow housing comprises a first engaging element and a second engaging element for coupling to the first engaging element, so that said hollow housing completely encircles the canal following implantation of said implantable apparatus.

3. An implantable apparatus of claim 2 wherein the first engaging element comprises a first cylindrical half shell and the second engaging element comprises a second cylindrical half shell movable from an open position to a closed position wherein the first and second cylinder half shells when coupled together form a hollow cylinder having an inner diameter adapted to generally fit around the canal.

4. An implantable apparatus of claim 3 wherein the first cylindrical half shell is pivotally connected to the second cylindrical half shell such that the second cylindrical half shell is movable from an open position to a closed position.

5. An implantable apparatus of claim 4 further comprising a locking member for locking the first and second cylindrical half shells into the locked position when the first and second cylindrical half shells are coupled together.

6. An implantable apparatus of claim 1 wherein said hollow housing comprises a generally cylindrical shape having an inner diameter suitable for surrounding a human urethra.

7. An implantable apparatus of claim 1, wherein said implantable apparatus further comprises a solenoid for activating said electrically operated piston.

8. An implantable apparatus of claim 7, wherein said implantable apparatus further includes a hollow casing connected perpendicular to said hollow housing for housing said electrically operated piston.

9. An implantable apparatus of claim 7, wherein said hollow housing further includes a mesh embedded therein to which a portion of the selected area of the canal is sutured following implantation thereof, so that said implantable device is anchored in place.

10. An implantable apparatus of claim 1, wherein the plunger includes a front face for engaging the canal, the front face having thereon more than one pressure point for contacting and applying pressure to the portion of the selected area of the canal when said electrically operated piston is engaged with the canal.

11. An implantable apparatus of claim 10, wherein the pressure points are in the form of ridges.

12. An implantable apparatus of claim 1, wherein said hollow housing comprises at least two cylindrical shells that fit together to form a hollow cylindrical casing wherein the cylindrical shells include a plurality of portals for allowing body fluids, from outside the canal, to flow into the hollow cylindrical casing.

13. An implantable apparatus of claim 1 wherein said control device comprises an electromagnetic field generator for generating an electromagnetic field comprising a code for activating said electrically operated piston.

14. An implantable apparatus of claim 1, wherein said control device comprises a magnet for activating said electrically operated piston, said control device further including a switch activated by the magnet being waved in the proximity of the switch to activate said electrically operated piston.

15. A method for controlling the flow of a body fluid within a canal in a host body comprising the steps of:
    making an incision in the host body at a selected location to provide access to a selected canal;
    placing an implantable body fluid control device having an electrically operated piston at a selected location around the selected canal to implant said implantable device inside the host body without severing the selected canal to implant said implantable device around the selected canal or operate said implantable device following said implantation thereof; and
    locking said implantable device in a closed position following said implantation, so that said constricting piston when operated engages and sufficiently constricts a selected portion of the selected canal to control the flow of the body fluid through the selected canal.

16. A method of claim 15, wherein said method further comprises removing the sphincter muscle from the host.

17. A method of claim 15, wherein said step of placing said implantable device at a selected location around the selected canal further comprises placing a first shell at the selected location around the selected canal and coupling a second shell to the first shell, so that said implantable device surrounds at least a portion of the selected canal.

18. An implantable fluid flow control device for fitting around a body tube without having to sever the body tube to implant said implantable device or to operate said implantable device following implantation thereof, said implantable device comprising:
    a first shell;
    a second shell;
    a hinge for pivotally coupling the first shell to the second shell to form a hollow assembly around the body tube having an open position and a closed position;
    a lock for locking said hollow assembly into the closed position;
    a constricting device for restricting fluid flow through the body tube; and
    a control device for selectively moving said constricting device between an extended position to constrict a portion of the selected area of the canal to reduce or stop fluid flow through the canal and a retracted positioned to open the constricted portion of the selected area of the canal to permit fluid flow through the canal, following the implantation of the implantable fluid flow control device.

19. An implantable device of claim 18, wherein said first and second shells include portals for permitting fluid from outside the canal to flow therethrough.

20. The device of claim 19, wherein said constricting device comprises a plunger and a solenoid for moving the plunger against the body tube to constrict the body tube when activated, so that fluid flow through the constricted body tube is restricted or stopped.

21. An implantable apparatus for controlling fluid flow through a canal within a host body without having to sever the canal to implant said implantable apparatus, said implantable apparatus comprising:
    an engaging component for engaging a canal within the body, the canal having a diameter, said engaging component comprising a plurality of portals for allowing body fluid flow outside the canal;
    a constricting element for restricting fluid flow through the canal when said constricting element is activated; and
    a control device for activating said constriction element to reduce the diameter of the canal.

22. An implantable apparatus of claim 21 wherein said control device includes a magnetic switch.

23. An implantable apparatus of claim 21, wherein said constricting element includes a sliding cylindrical shaft that reciprocates in a tubular housing.

24. A method for controlling the flow of a body fluid within a canal in a host body comprising the steps of:
    making an incision in the host body to provide access to a selected canal;
    placing a controllable constricting device around the selected canal without severing the selected canal;
    locking the controllable constricting device in a closed position, wherein the canal is engaged by the constricting device, so that, when the constricting device is activated, fluid flow through the selected canal is controlled; and
    removing the sphincter muscle from the host.

25. An implantable apparatus for selectively controlling fluid flow through a canal having internal and external walls and diameters, respectively, in a host body without having to sever the canal to implant said implantable apparatus in the host body or to operate said implantable apparatus following implantation thereof, said implantable apparatus comprising:
    a stop device positioned adjacent a selected portion of the external wall of a selected canal through which fluid flows following implantation of said implantable apparatus into the body host;
    an electrically operated constricting piston having a sliding plunger for engaging a certain area of the external wall of the selected canal which is opposite the selected area of the external wall against which said stop device is located when said constricting piston is activated; and
    a control device for selectively activating said electrically operated constricting piston,
    whereby, when said control device is activated, the plunger when retracted extends to an extended position to restrict the certain area of the exterior wall of the selected canal against said stop device to reduce the internal diameter of the selected canal located between the plunger and said stop device to reduce or stop fluid flow through the selected canal, and the plunger when extended retracts to a retracted position to open the selected canal to permit fluid flow there through.

26. An implantable device of claim 25 further comprising a hollow cylinder for surrounding the selected canal of which said stop device and said constricting piston are a part, said hollow cylinder having a plurality of portals for allowing fluid outside of the selected canal to flow through said portals.

27. An implantable device of claim 25, wherein said implantable device further includes a mesh embedded therein to which a portion of the selected canal is sutured following implantation thereof to anchor said implantable device.

28. An implantable incontinence apparatus for selectively controlling urine flow from a bladder through an urethra having internal and external walls and diameters, respectively, in a host body without having to sever the urethra to implant said implantable apparatus in the host body or to operate said implantable device following implantation thereof, said implantable apparatus comprising:

a hollow housing, wherein said hollow housing has a plurality of portals for permitting fluid from outside of the urethra to flow into said hollow housing to promote tissue growth and anchor said implantable incontinence device following implantation thereof, a stop device within said hollow housing and positioned adjacent a selected portion of the external wall of the urethra through which urine flows following implantation of said implantable incontinence apparatus into the body host;

an electrically operated constricting piston having a sliding shaft connected to a plunger for engaging a certain area of the external wall of the urethra which is opposite the selected area of the external wall of the urethra against which said stop device is located when said electrically operated constricting piston is activated, said plunger having a front on which more than one ridge is formed to create separate pressure points against the urethra when the plunger engages the urethra;

a control device for selectively activating said constricting piston;

whereby, when said control device is activated, the plunger when retracted extends to an extended position to restrict to restrict the certain area of the exterior wall of the urethra against said stop device to reduce the internal diameter of the urethra located between the plunger and said stop device to reduce or stop urine flow through the urethra, and the plunger when extended retracts to a retracted position to open the urethral to permit urine flow there through.

29. An incontinence implantable device of claim 28, wherein said implantable incontinence device further includes a mesh embedded therein to which the urethra is sutured following implantation thereof to anchor said implantable incontinence device.

30. An incontinence implantable device of claim 25, wherein said implantable incontinence device further includes a mesh embedded therein to which the urethra is sutured following implantation thereof to anchor said implantable incontinence device.

* * * * *